United States Patent [19]

Tabata et al.

[11] Patent Number: 5,233,099
[45] Date of Patent: Aug. 3, 1993

[54] PROCESS FOR PRODUCING ALCOHOL

[75] Inventors: Osamu Tabata; Kunizo Hashiba; Takahiro Kawakami, all of Wakayama, Japan

[73] Assignee: Kao Corporation, Tokyo, Japan

[21] Appl. No.: 812,825

[22] Filed: Dec. 24, 1991

[30] Foreign Application Priority Data

Dec. 27, 1990 [JP] Japan .................................. 2-408224
Sep. 11, 1991 [JP] Japan .................................. 3-231704

[51] Int. Cl.$^5$ .................. C07C 29/149; C07C 31/125
[52] U.S. Cl. ..................................... 568/885; 568/814; 568/836; 568/853; 568/864
[58] Field of Search ............... 568/885, 864, 836, 817, 568/853

[56] References Cited

U.S. PATENT DOCUMENTS

| | | | |
|---|---|---|---|
| 4,144,198 | 3/1979 | Miya et al. | 568/885 |
| 4,278,567 | 7/1981 | Miya et al. | 568/885 |
| 4,918,248 | 4/1990 | Hattori et al. | 568/885 |
| 4,982,020 | 1/1991 | Cardick et al. | 568/885 |

FOREIGN PATENT DOCUMENTS 0350763 1/1990 European Pat. Off. .

Primary Examiner—Joseph E. Evans
Attorney, Agent, or Firm—Sughrue, Mion, Zinn Macpeak & Seas

[57] ABSTRACT

A process for producing an alcohol by continuously passing a fatty acid ester, a fatty acid triglyceride or a fatty acid through a hydrogenation catalyst to thereby produce the aimed alcohol through catalytic reduction is disclosed, wherein the employed reactor is a fixed bed reactor in which the liquid phase and the gas phase are continuously passed together in descending parallel flows through the hydrogenation catalyst fixed in the reactor; and at least one cooling mean for cooling the reaction system is provided at a position in the vertical direction of the reactor. According to the process of the present invention with the use of a fixed bed reactor, an alcohol, which has extremely high qualities and a high purity and is contaminated with little hydrocarbon and aldehyde by-products, can be produced. The process of the present invention further makes it possible to omit the post-treatment for eliminating the by-products.

10 Claims, No Drawings

PROCESS FOR PRODUCING ALCOHOL

FIELD OF THE INVENTION

This invention relates to an improved process for producing a fatty alcohol which comprises catalytically reducing a fatty acid ester, a fatty acid triglyceride or a fatty acid continuously in the presence of a hydrogenation catalyst.

BACKGROUND OF THE INVENTION

A conventional method for producing a fatty alcohol comprises catalytically reducing a starting material selected from among natural fats and oils, fatty acids and fatty acid esters continuously.

This catalytic reduction is performed in the presence of a hydrogenation catalyst under a pressure of from 250 to 300 bar at a temperature of 200° C. or above under an excess hydrogen atmosphere.

Since a reduction of a fatty acid ester, a fatty acid triglyceride or a fatty acid is an exothermic reaction, when an alcohol is produced by catalytically reducing such fatty acid ester, fatty acid triglyceride or fatty acid with a fixed bed reactor, the reaction has been carried out under apparently isothermal conditions with liberating the heat generated during the course of the reaction in order to improve qualities of the alcohols thus produced, as disclosed in JP-A-64-47725 (corresponding to U.S. Pat. No. 5,043,485), JP-A-63-39829 (corresponding to U.S. Pat. No. 4,982,020) and JP-A-1-275542 (corresponding to U.S. Pat. No. 4,942,266) (the term "JP-A" as used herein means an "unexamined published Japanese patent application") and U.S. Pat. No. 4,855,273 and U.S. Pat. No. 4,935,556.

When such a catalytic reduction for producing an alcohol is continuously performed with a fixed bed reactor, it is important to prolong the life of the catalyst, since the performance of the device and the productivity significantly depend on the life of the catalyst. In the conventional method wherein the temperature in a reactor is maintained under apparently isothermal conditions, the formation of by-products such as hydrocarbons and aldehydes in the alcohol product can be suppressed. When the catalytic reduction is continuously carried out in a reactor in which a catalyst is fixed (e.g., a fixed bed reactor), on the other hand, the catalytic activity lowers as the operation time is prolonged and thus it is required to elevate the reaction temperature so as to maintain the conversion ratio. However, when the reaction temperature is elevated, the formation of the by-products tends to increase.

The life of the catalyst is mainly influenced by the conversion ratio and the amounts of impurities and by-products. Thus the qualities of the alcohol product would be gradually deteriorated, even though the catalytic reduction is performed under apparently isothermal conditions. Namely, it is difficult to continuously obtain an alcohol of high qualities over a long period of time.

In the aforesaid conventional methods, the reaction is performed under approximately isothermal conditions. Therefore an alcohol of high qualities can hardly be obtained, as the deterioration of the catalyst proceeds.

Further, it is required to eliminate hydrocarbons or aldehydes formed by the excessive reaction, since the qualities of the alcohol are deteriorated by these by-products. The boiling point ranges of the hydrocarbons overlap these of short-chain alcohols and thus the starting material must be fractionated by, for example, distillation prior to the reaction. On the other hand, the aldehydes are converted into fatty alcohols of the corresponding chain length by treating with, for example, a chemical such as a reducing agent. These treatments make the procedure complicated and cause an increase in the production cost.

Therefore it has been required to develop a process for producing an alcohol by using a fixed bed reactor in which the life of the fixed bed catalyst can be prolonged and a fatty alcohol of high qualities and a high purity can be continuously produced over a long period of time.

SUMMARY OF THE INVENTION

Under these circumstances, the present inventors have found that, in a process for producing a fatty alcohol by catalytically reducing a fatty acid ester, a fatty acid triglyceride or a fatty acid (hereinafter sometimes abbreviated as "starting material" or "starting oil") in the presence of a hydrogenation catalyst, a fatty alcohol of extremely high qualities and a high purity can be continuously produced over a long period of time while keeping a long life of a fixed bed catalyst and requiring no post-treatment of the product by using a fixed bed reactor and controlling the temperature in the reactor so as to precisely control the temperature in the reactor, thus completing the present invention.

Accordingly, the present invention provides a process for producing an alcohol which comprises:

continuously feeding a starting material selected from a fatty acid ester, a fatty acid triglyceride and a fatty acid and hydrogen into a fixed bed reactor in which a hydrogenation catalyst is packed, hydrogen being fed at about 20 to about 300 bar and the starting material being fed in such a manner as to give a molar ratio of hydrogen to the fatty acid group of the starting material of from about 5:1 to about 500:1;

passing the starting material and hydrogen through the hydrogenation catalyst in descending parallel flows; and then recovering the alcohol, wherein the reactor is provided with at least one cooling means for cooling the reaction system at a position in the vertical direction thereof and a temperature of a zone in the reactor where a conversion ratio of the starting material exceeds about 60% is controlled to 100° to 220° C. by the cooling means, provided that a maximum temperature of a zone in the reactor where a conversion ratio of the starting material is about 60% or below is at least 10° C. higher than a minimum temperature of the zone in the reactor where a conversion ratio exceeds about 60%, and that a minimum temperature of the zone where a conversion ratio of the starting material is about 60% or below is higher than the minimum temperature of the zone where a conversion ratio of the starting material exceeds about 60%.

DETAILED DESCRIPTION OF THE INVENTION

The fixed bed reactor to be used in the present invention is provided with at least one cooling means for cooling the reaction system (a liquid, a gas and a solid) at a position in the vertical direction thereof.

As the fixed bed reactor itself, those conventionally used in the art may be used in the present invention. Examples of the fixed bed reactor include those comprising a single fixed bed and those of which plural fixed beds are provided in series as a multistage. In the latter case, the cooling means may be provided between the fixed beds. Details of the fixed bed reactors may be seen, for example, in *THE OIL AND GAS JOURNAL*, May 16, 1966, pages 173-178 (1966) and *HYDROCARBON PROCESSING*, November 1970, pages 187-191 (1970).

As the cooling means, either a direct cooling means using quench hydrogen, a quench oil or an inert quench substance, an indirect cooling means using a coolant, or a combination of the direct cooling means and the indirect cooling means may be employed in the present invention. Details of the cooling means may be seen, for example, in Stanley M. Walas, *Chemical Process Equipment*, published by Butterworth Publishers, pages 572-579 (1988); *Chemical Economy & Engineering Review*, vol 3, No. 9 (No. 41), pages 14-28 (1971); *Ind. Eng. Chem. Process Des. Dev.*, vol. 15, No. 3, pages 400-406 (1976); *Ind. Eng. Chem. Process Des. Dev.*, vol. 17, No. 1, Page 27 et seq. (1978); Howard F. Rase, *CHEMICAL REACTOR DESIGN FOR PROCESS PLANTS*, published by A WILEY-INTERSCIENCE PUBLICATION, volume two, pages 61-84 (1977).

The position and the number of the cooling means and the amount of quench hydrogen, the quench oil, the inert quench substance or the coolant may be determined depending on the kind of the hydrogenation catalyst, the activity of the hydrogenation catalyst, the reaction temperature, the molar ratio of hydrogen to the fatty acid group of the starting material and the kind and flow rate of the starting material.

In the process of the present invention, the above-mentioned reactor is employed and temperatures in the reactor are controlled. A temperature in the zone of the reactor where the conversion ratio exceeding about 60% is controlled to 100° to 220° C., preferably 100° to 190° C. and more preferably 100° to 160° C., whereby the reaction can be mildly performed in the zone. Thus the amounts of by-products such as hydrocarbons and aldehydes can be suppressed at an extremely low level. When the temperature in the zone where the conversion ratio exceeds about 60% is maintained at higher than 220° C., the formation of the by-products tends to be undesirably promoted. When the temperature in the zone where the conversion ratio exceeds about 60% is maintained at lower than 100° C., on the other hand, the conversion ratio tends to be undesirably lowered. The temperature in some part in the zone where the conversion ratio exceeds 60% in the reactor may be outside the temperature range as specified above, so long as the effects of the present invention are not deteriorated thereby.

In the zone where the conversion ratio is 60% or below, the reaction temperature may arbitrarily be determined depending on the conversion ratio based on the kind of the hydrogenation catalyst, the hydrogenation activity of the catalyst, the molar ratio of hydrogen to the fatty acid group of the starting material and the kind and flow rate of the starting material. Preferably, it is controlled to 150° to 300° C. and more preferably it is controlled to 170° to 280° C.

The conversion ratio and the composition of the starting material and the reaction products in the reactor can be determined by analyzing the reaction system. Alternately, it may easily be estimated by a common calculation method, i.e., through the calculation of the material balance and the heat balance by taking the gas/liquid equilibrium, chemical reaction rate and the physicochemical phenomena in the reactor into consideration. Sampling of the reaction system can be conducted through sampling nozzles provided at positions in the vertical direction of the reactor. Further, in the case of the reactor of which plural fixed beds are provided in series, sampling of the reaction system can be conducted through a nozzle provided at a transport line between the fixed beds. An alcohol, a hydrocarbon, a fatty acid ester, a glyceride, a fatty acid and carbon monoxide in the reaction system can be analyzed by gas chromatography, while an aldehyde can be analyzed by a method according to JIS K 1525-1960 (the term "JIS" as used herein means "Japanese Industrial Standard") or in a manner as disclosed, for example, in A. S. Henick et al, *J. Am. Oil Chemists Socy.*, vol. 31, 88 (1954) and Shinji Mitsunaga et al., *Oil Chemistry*, vol. 7, (5), 275 (1958). The calculation method may be seen, for example, in Shigeo Goto, *AIChE Journal*, vol. 21, No. 4, page 706 (1975); ibid, page 714; and Giorgio Soave, *Chemical Engineering Science*, vol. 27, pages 1197-1203 (1972).

In the process of the present invention, the cooling is effected so as to give the difference between the maximum temperature of the reactor where the conversion ratio is about 60% or below (T1) and the minimum temperature of the zone where the conversion ratio exceeding 60% (T2) of at least 10° C., preferably at least 20° C. and more preferably at least 30° C., provided that T1 is higher than T2. The cooling is also effected so as to control the minimum temperature of the zone of the conversion ratio of about 60% or below is higher than the minimum temperature of the zone of the conversion ratio exceeding about 60%. The difference between the minimum temperature of the zone of the conversion ratio of about 60% or below and the minimum temperature of the zone of the conversion ratio exceeding about 60% is preferably controlled to at least 5° C., more preferably 10° C., furthermore preferably 20° C. and still furthermore preferably 40° C. As the catalytic activity decreases, larger differences between the minimum temperature of the zone of the conversion ratio exceeding about 60% and the maximum and minimum temperatures of the zone of the conversion ratio of about 60% or below are more advantageous.

These temperature controls make it possible to elevate the temperature in the zone of the conversion ratio of about 60% or below as the catalytic activity decreases, whereby the definite conversion ratio is maintained without increasing the amount of the by-products. Thus, an alcohol of high qualities can continuously produced over long period of time in the process of the present invention.

The temperature at the inlet of the reactor may be freely determined so as to achieve the definite conversion ratio.

In the process of the present invention, the starting material and hydrogen are fed into the fixed bed reactor in a manner so as to give a molar ratio of hydrogen to the fatty acid group of the starting material of from about 5:1 to about 500:1, preferably from about 10:1 to about 200:1, more preferably from about 15:1 to about 100:1.

Although flow rate of the starting material in the process of the present invention may vary depending on the kind of the hydrogenation catalyst employed, the activity of the hydrogenation catalyst, the reaction temperature, the molar ratio of hydrogen to the fatty acid group of the starting material and the kind of the starting material, it may be controlled so as to give a volume ratio to the reactor per hour (liquid hourly space velocity, hereinafter abbreviated as LHSV) of about 0.05 to 20 l/hr, preferably about 0.1 to 10 l/hr and more preferably about 0.2 to 5 l/hr.

The starting fatty acid ester to be used in the process of the present invention is a straight-chain or branched and saturated or unsaturated fatty acid ester containing one or more alcohol residues having one or more carbon atoms. Further, alicyclic carboxylic esters and aromatic carboxylic esters may be used therefor.

Examples of the aforesaid alcohol residue include residues of straight- or branched-chain alcohols having 1 to carbon atoms such as methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol and trimethylolpropane.

The aforesaid fatty acid esters and carboxylic esters are not particularly restricted. Examples thereof include formates, acetates, caproates, caprates, undecenoates, laurates, myristates, palmitates, stearates, isostearates, oleates, oxalates, maleates, adipates, sebacates, cyclohexanecarboxylates, benzoates and phthalates.

Examples of the starting fatty acid triglyceride include coconut oil, palm oil, palm kernel oil, soybean oil, rapeseed oil, cottonseed oil, olive oil, beef tallow and fish oil.

As the starting fatty acid, those constituting the aforesaid fatty acid esters and fatty acid triglycerides may be cited.

Among these starting materials, fatty acid methyl ester is widely used.

Further, the fatty acid ester or fatty acid may be separated into fractions by, for example, distillation. Furthermore, the starting fatty acid ester, fatty acid triglyceride or fatty acid may be subjected to a pretreatment prior to the hydrogenation, so as to eliminate impurities contained therein. For example, sulfur, nitrogen, phosphorus and halogens may be eliminated from the starting material with the use of a guard reactor packed with a catalyst for removing impurities or distillation, extraction or a combination of these procedures.

The catalyst useful in the process of the present invention may be a known one commonly used in hydrogenation such as a Cu-Cr catalyst as disclosed, for example, in *Industrial and Engineering Chemistry*, vol. 26, page 878 (1936); Cu-Zn catalyst as disclosed, for example, in JP-A-63-141937, JP-A-2-36135 and JP-A-2-157044; Cu-Fe-Al catalyst as disclosed, for example, in JP-B-58-50775 (the term "JP-B" as used herein means "examined Japanese Patent Publication"); and Cu-Zn-Ti catalyst as disclosed, for example, in JP-A-1-305042. The catalyst is in the form of either granules or tablets suitable for packing in the fixed bed reactor.

According to the process of the present invention, the content of hydrocarbon by-products in the obtained fatty alcohol can be reduced to 0.5% or less, preferably 0.3% or less and more preferably 0.1% or less. This is because the formation of the hydrocarbon by-products can be controlled by precisely adjusting the production ratio of the alcohol, the reaction temperature and pressure.

According to the present invention, it is also possible to reduce the content of aldehyde by-products in the obtained fatty alcohol to 30 ppm or less, preferably 10 ppm or less and more preferably 3 ppm or less. This is because these aldehyde would be converted into the corresponding alcohols when they are reacted in the presence of a hydrogenation catalyst under a hydrogen atmosphere at a low temperature.

Furthermore, it is possible to lower the content of carbon monoxide contained in the excess hydrogen in the reactor. This carbon monoxide exerts no effect on the qualities of the alcohol. When the excess hydrogen containing carbon monoxide is recovered and reused, however, carbon monoxide acts as poison to the employed hydrogenation catalyst and thus the catalytic activity is deteriorated. This phenomenon brings about a serious problem, especially, in a fixed bed reactor. The aforesaid carbon monoxide can be converted into methanol in the reaction in the presence of a hydrogenation catalyst under a hydrogen atmosphere at a low temperature. Thus the carbon monoxide content in an excess hydrogen from the reactor can be reduced to 1,000 ppm or less, preferably 200 ppm or less and more preferably 10 ppm or less, by controlling the temperature as described above.

To further illustrate the present invention, and not by way of limitation, the following Examples will be given.

The fatty acid esters, fatty acid triglycerides and fatty acids used in these Examples were undistilled ones.

EXAMPLES 1 AND 2 AND COMPARATIVE EXAMPLES 1 AND 2

A reactor (internal diameter: 25 mm; height: 2,000 mm) was packed with 500 cc of a commercially available Cu-Cr catalyst pellets (diameter: 3 mm) (N202D, manufactured by NIKKI CHEMICAL Co., Ltd.). After activating the catalyst by reducing, coconut oil methyl ester was continuously fed thereto together with hydrogen at 230 bar in a descending flow, thus effecting a reaction.

Quench hydrogen was introduced into the reactor at points of ½ and 2/4 from the top so as to control the temperature in the reactor and the outlet temperature.

In Comparative Examples, the procedure was carried out under approximately isothermal conditions.

Table 1 shows the reaction conditions and the analytical data of the product obtained in each case.

TABLE 1

|  | Example 1 | Example 2 | Comparative Example 1 | Comparative Example 2 |
| --- | --- | --- | --- | --- |
| Inlet temperature (°C.) | 220 | 240 | 220 | 240 |
| Maximum temperature of zone of conversion ratio of 60% or below (T1) (°C.) | 230 | 245 | 222 | 245 |
| Minimum temperature of zone of conversion ratio of 60% or below (°C.) | 220 | 240 | 220 | 240 |
| Minimum temperature of zone of conversion ratio exceeding 60% (T2) (°C.) | 150 | 200 | 220 | 240 |

TABLE 1-continued

|  | Example 1 | Example 2 | Comparative Example 1 | Comparative Example 2 |
|---|---|---|---|---|
| Difference in temperature in reactor (T1-T2) (°C.) | 80 | 45 | 2 | 5 |
| Liquid hourly space velocity (LHSV) (l/hr) | 1 | 2 | 1 | 2 |
| Molar ratio of inlet feed hydrogen to fatty acid group | 60 | 40 | 100 | 70 |
| Molar ratio of first quench hydrogen to fatty acid group | 20 | 10 | 2 | 3 |
| Molar ratio of second quench hydrogen to fatty acid group | 10 | 5 | 2 | 3 |
| Saponification value (KOH mg/g) | 2 | 3 | 2 | 3 |
| Hydrocarbon (% by weight) | 0.00 | 0.08 | 0.52 | 0.70 |
| Aldehyde (ppm) | 3 | 10 | 35 | 80 |
| CO concentration in circulating hydrogen (ppm) | 3 | 30 | 100 | 1100 |

Note:
The conversion ratio (%) was defined in the following equation:

$(1 - SV/SV_0) \times 100$ wherein SV means the saponification value of the reaction product, and $SV_0$ means the saponification value of the starting material.

The analytical data of the starting coconut oil methyl ester were as follows:
 Saponification value: 255
 Acid value: 0.1
 Hydroxyl value: 0.1.

As Table 1 shows, the amounts of the by-products in Examples 1 and 2 were extremely small, while obviously larger amounts of the by-products were formed in Comparative Examples 1 and 2.

EXAMPLE 3 AND COMPARATIVE EXAMPLE 3

By using the same reactor and the same catalyst as those employed in Examples 1 and 2, coconut oil triglyceride was continuously fed together with hydrogen at 230 bar in a descending flow to thereby effect a catalytic reduction.

In Comparative Example 3, the procedure was carried out under approximately isothermal conditions.

Table 2 shows the reaction conditions and the analytical data of the product obtained in each case.

The reaction ratio was defined in the same manner as in Examples 1 and 2.

TABLE 2

|  | Example 3 | Comparative Example 3 |
|---|---|---|
| Inlet temperature (°C.) | 220 | 210 |
| Maximum temperature of zone of conversion ratio of 60% or below (T1) (°C.) | 230 | 213 |
| Minimum temperature of zone of conversion ratio of 60% or below (°C.) | 220 | 210 |
| Minimum temperature of zone of conversion ratio exceeding 60% (T2) (°C.) | 190 | 210 |
| Difference in temperature in reactor (T1-T2) (°C.) | 40 | 3 |
| Liquid hourly space velocity (LHSV) (l/hr) | 0.5 | 0.5 |
| Molar ratio of inlet feed hydrogen to fatty acid group | 40 | 80 |
| Molar ratio of first quench hydrogen to fatty acid group | 30 | 4 |
| Molar ratio of second quench hydrogen to fatty acid group | 20 | 2 |
| Saponification value (KOH mg/g) | 3 | 2 |
| Hydrocarbon (% by weight) | 0.25 | 0.55 |
| Aldehyde (ppm) | 10 | 40 |
| CO concentration in circulating hydrogen (ppm) | 5 | 30 |

The analytical data of the starting coconut oil triglyceride were as follows:
 Saponification value: 245
 Acid value: 0.1
 Hydroxyl value: 0.1

As Table 2 shows, the amounts of the by-products in Example 3 were extremely small, while obviously larger amounts of hydrocarbons and aldehydes were formed in Comparative Example 3.

EXAMPLE 4 AND COMPARATIVE EXAMPLE 4

By using the same reactor and the same catalyst as those employed in Examples 1, 2 and 3, a coconut oil fatty acid was continuously fed together with hydrogen at 230 bar in a descending flow to thereby effect a catalytic reduction.

In Comparative Example 4, the procedure was carried out under approximately isothermal conditions.

Table 3 shows the reaction conditions and the analytical data of the product obtained in each case.

The conversion ratio (%) was defined as:

$(1 - AB/AV_0) \times 100$ wherein AV means the acid value of the reaction product and $AV_0$ means the acid value of the starting material.

TABLE 3

|  | Example 4 | Comparative Example 4 |
|---|---|---|
| Inlet temperature (°C.) | 220 | 215 |
| Maximum temperature of zone of conversion ratio of 60% or below (T1) (°C.) | 235 | 220 |
| Minimum temperature of zone of conversion ratio of 60% or below (°C.) | 220 | 215 |
| Minimum temperature of zone of conversion ratio exceeding 60% (T2) (°C.) | 190 | 215 |
| Difference in temperature in | 45 | 5 |

TABLE 3-continued

|  | Example 4 | Comparative Example 4 |
|---|---|---|
| reactor (T1-T2) (°C.) |  |  |
| Liquid hourly space velocity (LHSV) (l/hr) | 1 | 1 |
| Molar ratio of inlet feed hydrogen to fatty acid group | 40 | 80 |
| Molar ratio of first quench hydrogen to fatty acid group | 30 | 6 |
| Molar ratio of second quench hydrogen to fatty acid group | 10 | 2 |
| Acid value (KOH mg/g) | 3 | 3 |
| Hydrocarbon (% by weight) | 0.30 | 0.60 |
| Aldehyde (ppm) | 10 | 50 |
| CO concentration in circulating hydrogen (ppm) | 5 | 60 |

The analytical data of the starting coconut oil fatty acid were as follows:
Acid value: 265
Iodine value: 8.5.

As Table 3 shows, the amounts of the by-products in Example 4 were extremely small, while obviously larger amounts of by-products were formed in Comparative Example 4.

An alcohol, which has extremely high qualities and a high purity and contains little hydrocarbon and aldehyde by-products, can be produced using a fixed bed reactor in the process accordance with the present invention.

Further, the process of the present invention makes it possible to omit a post-treatment for removing the by-products.

While the invention has been described in detail and with reference to specific examples thereof, it will be apparent to one skilled in the art that various changes and modifications can be made therein without departing from the spirit and scope thereof.

What is claimed is:

1. A process for producing an alcohol which comprises:
   continuously feeding a starting material selected from the group consisting of a fatty acid ester and a fatty acid with hydrogen into a fixed bed reactor in which a hydrogenation catalyst is packed, hydrogen being fed at about 20 to 300 bar and the starting material being fed in such a manner as to give a molar ratio of hydrogen to the fatty acid group of the starting material of from about 5:1 to about 500:1;
   passing the starting material and hydrogen through the hydrogenation catalyst in descending parallel flows; and then
   recovering the alcohol,
   wherein said reactor is provided with at least one cooling means for cooling the reaction system at a position in the vertical direction thereof and a temperature of a second zone in said reactor where a conversion ratio of the starting material exceeds about 60% is controlled to 100° to 220° C. by said cooling means, provided that a maximum temperature of a first zone in said reactor which precedes said second zone and where a conversion ratio of the starting material is about 60% or below is 150° to 300° C. and is at least 10° c. higher than a minimum temperature of said second zone in said reactor where the conversion ratio exceeds about 60%, and that a minimum temperature of said first zone where the conversion ratio of the starting material is about 60% or below is higher than said minimum temperature of said second zone, where the conversion ratio of the starting material exceeds about 60%, wherein a content of hydrocarbon by-products in said recovered alcohol is controlled to about 0.5% by weight or below, a content of aldehyde by-products in said recovered alcohol is controlled to 30 ppm or less, and a content of carbon monoxide in an excess hydrogen gas from the reactor is controlled to 1,000 ppm or less.

2. A process of claim 1, wherein said temperature of said second zone where the conversion ratio of the starting material exceeds about 60% is controlled to 100° to 190° C., wherein a content of hydrocarbon by-products in said recovered alcohol is controlled to about 0.3% by weight or below, a content of aldehyde by-products in said reconverted alcohol is controlled to 10 ppm or less, and a content of carbon monoxide in an excess hydrogen gas from the reactor is controlled to 200 ppm or less.

3. A process of claim 1, wherein said temperature of said second zone where the conversion ratio of the starting material exceeds about 60% is controlled to 100° to 16020 C., wherein a content of hydrocarbon by-products in said recovered alcohol is controlled to about 0.1% by weight or below, a content of aldehyde by products in said recovered alcohol is controlled to 3 ppm or less, and a content of carbon monoxide in an excess hydrogen gas from the reactor is controlled to 10 ppm or less.

4. A process of claim 1, wherein said minimum temperature of said first zone where the conversion ratio of the starting material is about 60% or below is at least 10° C. higher than said minimum temperature of said second zone where the conversion ratio of the starting material exceeds 60%.

5. A process of claim 1, wherein said minimum temperature of said first zone where the conversion ratio of the starting material is about 60% or below is at least 20° C. higher than said minimum temperature of said second zone where the conversion ratio of the starting material exceeds 60%.

6. A process of claim 1, wherein said starting material is a fatty acid methyl ester.

7. A process of claim 1, wherein said hydrogenation catalyst is Cu-Zn-Ti catalyst.

8. A process of claim 1, wherein said hydrogenation catalyst is Cu-Fe-Al catalyst.

9. A process of claim 1, wherein said hydrogenation catalyst is Cu-Cr catalyst.

10. A process of claim 1, wherein said fatty acid ester is a fatty acid triglyceride.

* * * * *